United States Patent [19]

Kranz et al.

[11] 4,386,953
[45] Jun. 7, 1983

[54] HERBICIDALLY ACTIVE SUBSTITUTED 6-HALOGENO-TERT.-BUTYL-1,2,4-TRIAZIN-5-ONES

[75] Inventors: Eckart Kranz, Wuppertal; Kurt Findeisen, Odenthal; Robert Schmidt, Bergisch-Gladbach; Ludwig Eue, Leverkusen, all of Fed. Rep. of Germany

[73] Assignee: Bayer Aktiengesellschaft, Leverkusen, Fed. Rep. of Germany

[21] Appl. No.: 299,919

[22] Filed: Sep. 8, 1981

[30] Foreign Application Priority Data

Oct. 2, 1980 [DE] Fed. Rep. of Germany ....... 3037300

[51] Int. Cl.³ .................. C07D 253/06; A01N 43/64
[52] U.S. Cl. ........................................ 71/93; 544/182
[58] Field of Search ............................ 544/182; 71/93

[56] References Cited

U.S. PATENT DOCUMENTS

| | | | |
|---|---|---|---|
| 3,671,523 | 6/1972 | Westphal et al. | 544/182 |
| 3,905,801 | 12/1975 | Fawzi | 544/182 |
| 3,961,936 | 6/1976 | Westphal et al. | 544/182 |
| 4,036,632 | 7/1977 | Westphal et al. | 71/93 |
| 4,309,538 | 1/1982 | Schmidt et al. | 544/182 |
| 4,315,094 | 2/1982 | Bonse et al. | 544/182 |
| 4,346,220 | 8/1982 | Fawzi | 544/182 |

FOREIGN PATENT DOCUMENTS

| | | |
|---|---|---|
| 2165554 | 7/1973 | Fed. Rep. of Germany . |
| 2726016 | 1/1979 | Fed. Rep. of Germany . |
| 1577658 | 8/1969 | France . |
| 1182801 | 3/1970 | United Kingdom . |
| 1182802 | 3/1970 | United Kingdom . |

Primary Examiner—John M. Ford
Attorney, Agent, or Firm—Sprung, Horn, Kramer & Woods

[57] ABSTRACT

A substituted 6-halogeno-tert.-butyl-1,2,4-triazin-5-one of the formula

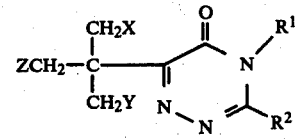

in which
R$^1$ is an amino or methyl group,
R$^2$ is an alkylmercapto, alkylamino or dialkylamino group,
X is a halogen atom, and
Y and Z each independently is a hydrogen or halogen atom, which possesses selective herbicidal activity. A synthesis involving the novel intermediates

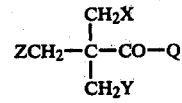

in which
X, Y and Z have the above-mentioned meaning and
Q is CN, CONH$_2$ or COOH,
is also shown.

12 Claims, No Drawings

HERBICIDALLY ACTIVE SUBSTITUTED 6-HALOGENO-TERT.-BUTYL-1,2,4-TRIAZIN-5-ONES

The present invention relates to certain new 6-halogeno-tert.-butyl-1,2,4-triazin-5-ones, to a process for their production and to their use as herbicides, in particular as selective herbicides.

It has already been disclosed that substituted 1,2,4-triazin-5-ones, such as, in particular, 4-amino-3-methylmercapto-6-tert.-butyl-1,2,4-triazin-5-one, can be used as herbicides (see, for example, German Patent Specification No. 1,795,784 and U.S. Pat. No. 3,671,523). However, it is not possible for the triazinones which are already known to be used selectively in certain crops, since damage can also occur to certain useful plants as a result of the consistently high herbicidal potency of this group of substances; accordingly, the tolerance of various crop plants to the triazinones which are already known is inadequate.

The present invention now provides, as new compounds, the substituted 6-halogeno-tert.-butyl-1,2,4-triazin-5-ones of the general formula $$\begin{array}{c} CH_2X \\ | \\ ZCH_2-C-\cdots \\ | \\ CH_2Y \end{array} \begin{array}{c} O \\ \| \\ C \\ \| \\ N \end{array} \begin{array}{c} R^1 \\ \diagdown N \\ \diagup \\ R^2 \end{array} \quad (I)$$

in which
- $R^1$ represents an amino or methyl group,
- $R^2$ represents an alkylmercapto, alkylamino or dialkylamino group,
- X represents a halogen atom and
- Y and Z independently represent a hydrogen or halogen atom.

According to the present invention there is further provided a process for the production of a compound of the present invention, characterised in that, in a first stage, a halogeno-pivaloyl cyanide of the general formula $$\begin{array}{c} CH_2X \\ | \\ ZCH_2-C-CO-CN \\ | \\ CH_2Y \end{array} \quad (II)$$

in which
X, Y and Z have the abovementioned meaning, is reacted with an inorganic acid, if appropriate in the presence of a liquid carboxylic acid, as the solvent, and the halogenated trimethylpyruvic acid amide thereby formed, of the general formula $$\begin{array}{c} CH_2X \\ | \\ ZCH_2-C-CO-CO-NH_2 \\ | \\ CH_2Y \end{array} \quad (IIIa)$$

in which
X, Y and Z have the abovementioned meaning, is reacted in a second stage, either directly in the solution obtained or after intermediate isolation, if appropriate after prior hydrolysis to give the free halogenated trimethylpyruvic acid of the general formula $$\begin{array}{c} CH_2X \\ | \\ ZCH_2-C-CO-COOH \\ | \\ CH_2Y \end{array} \quad (IIIb)$$

in which
X, Y and Z have the abovementioned meaning, with a compound of the general formula $$S=C\begin{array}{c} NH-R^1 \\ \diagdown \\ NH-NH_2 \end{array} \quad (IV)$$

in which
$R^1$ has the abovementioned meaning, in aqueous or in aqueous-acid solution, if appropriate in the presence of an organic diluent, to give a 6-halogeno-tert.-butyl-3-mercapto-1,2,4-triazin-5-one of the general formula $$\begin{array}{c} CH_2X \\ | \\ ZCH_2-C-\cdots \\ | \\ CH_2Y \end{array} \begin{array}{c} O \\ \| \\ C \\ \| \\ N \\ \diagdown N \\ | \\ H \end{array} \begin{array}{c} R^1 \\ \diagup \\ S \end{array} \quad (V)$$

in which
$R^1$, X, Y and Z have the abovementioned meaning, the compound of formula (V) is alkylated in a third stage by means of an alkyl halide, preferably an alkyl iodide or bromide, in alkaline solution to give a 6-halogeno-tert.-butyl-1,2,4-triazin-5-one of the general formula $$\begin{array}{c} CH_2X \\ | \\ ZCH_2-C-\cdots \\ | \\ CH_2Y \end{array} \begin{array}{c} O \\ \| \\ C \\ \| \\ N \\ \diagdown N \end{array} \begin{array}{c} R^1 \\ \diagup \\ S-R^3 \end{array} \quad (Ia)$$

in which
$R^1$, X, Y and Z have the abovementioned meaning and
$R^3$ represents an alkyl group, preferably 1 to 4 carbon atoms,
and, if a compound of formula (I) in which $R^2$ denotes an alkylamino or dialkylamino group is required, the compound of formula (Ia) is reacted in a fourth stage with an amine of the general formula $$HNR^4R^5 \quad (VI)$$

in which
- $R^4$ represents a hydrogen atom or an alkyl group, preferably with 1 to 4 carbon atoms, and
- $R^5$ represents an alkyl group, preferably with 1 to 4 carbon atoms, in the presence of a diluent.

It has also been found that the substituted 6-halogeno-tert.-butyl-1,2,4-triazin-5-ones of the present invention have good herbicidal properties, in particular good selective herbicidal properties.

Surprisingly, compared with the known compound 4-amino-3-methylmercapto-6-tert.-butyl-1,2,4-triazin-5-one, which is the closest related compound chemically and from the point of view of its action, the compounds according to the invention, while having an equally good general herbicidal action, are significantly better tolerated by important crop plants, such as, in particular, maize, cotton and cereal. The active compounds according to the invention thus represent a considerable enrichment of herbicidal agents, and in particular of selective chemical combating of weeds.

Preferred substituted 6-halogeno-tert.-butyl-1,2,4-triazin-5-ones according to the present invention are those in which $R^2$ represents a straight-chain or branched alkyl-mercapto group with 1 to 4 carbon atoms, or an alkyl- or dialkylamino group with in each case 1 to 6 carbon atoms in each alkyl part, and $R^1$, X, Y and Z have the meanings given above.

Those compounds of the formula (I) in which $R^1$ represents an amino or methyl group, $R^2$ represents a methyl-, ethyl- or propyl-mercapto group, or a methyl-, ethyl-, propyl-, hexyl-, dimethyl-, diethyl- or ethylmethyl-amino group, X represents a fluorine, chlorine or bromine atom, and Y and Z independently represent a hydrogen, fluorine, chlorine or bromine atom, are to be singled out as particularly preferred.

If, for example, chloropivaloyl cyanide is used as the starting substance in the first stage, the corresponding free acid is reacted with thiocarbohydrazide in the second stage and methyl bromide is used as the alkylating agent in the third stage, the course of the reaction according to the invention is illustrated by the following equation:

description of the particularly preferred compounds according to the invention.

The halogenopivaloyl cyanides of the formula (II) are novel. They are obtained by a process in which the corresponding halogenopivaloyl halide or anhydride of the formula

or

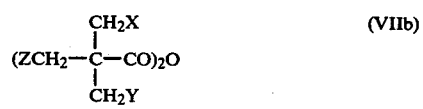

in which
Hal represents a halogen atom, preferably a chlorine or bromine atom, and
X, Y and Z have the abovementioned meanings,
is reacted with trimethylsilyl cyanide, if appropriate in the presence of a diluent. Trimethylsilyl cyanide, $(CH_3)_3Si\text{-}CN$, is known (see, for example, Synthesis 1979, pages 522 and 523).

If appropriate, this process for the preparation of the halogenopivaloyl cyanides of the formula (II) is carried out in the presence of a diluent. Diluents include, preferably, inert organic solvents, such as ketones (for ex-

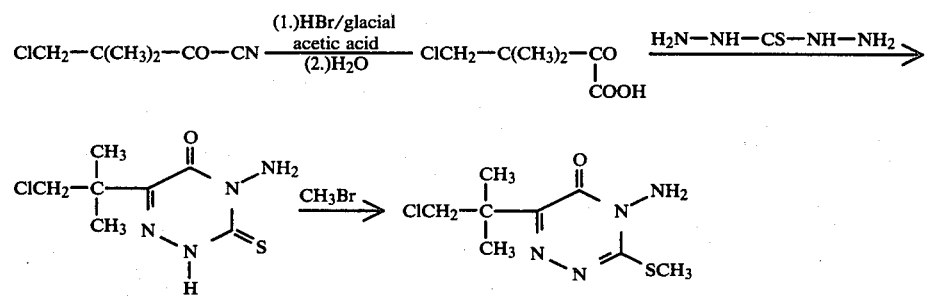

If the 4-amino-6-chloro-tert.-butyl-3-methylmercapto-1,2,4-triazin-5-one thus obtained and dimethylamine are used as starting substances for the fourth stage, the course of this stage of the reaction according to the invention is illustrated by the following equation:

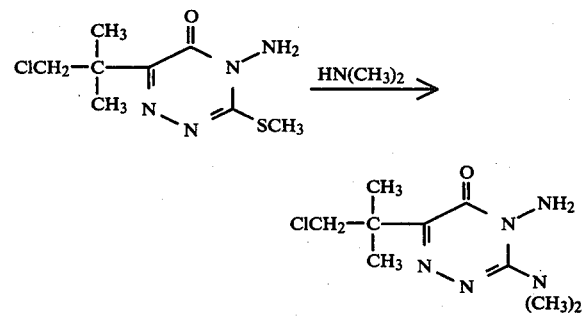

Preferred halogenopivaloyl cyanides of formula (II) to be used as starting substances for the process according to the invention are those in which X, Y and Z represent those radicals which have already been mentioned for these substituents in connection with the ample acetone and methyl ethyl ketone), nitriles (for example acetonitrile), ethers (for example tetrahydrofuran or dioxane) and aromatic hydrocarbons (for example benzene, toluene or xylene).

The process is preferably carried out without a solvent.

The reaction temperatures can be varied within a substantial range in carrying out this process. In general, the reaction is carried out at a temperature between 50° and 250° C., preferably between 80° and 180° C.

Equivalent amounts of starting substances are preferably used in carrying out this process. The compounds of the formula (II) are isolated in the customary manner.

Halogenopivaloyl halides and anhydrides of the formulae (VIIa) and VIIb) respectively are known, and they can be obtained in a generally known manner.

The first stage of the process according to the invention can be carried out in the absence or in the presence of an aliphatic carboxylic acid, as the solvent, which is liquid under the reaction conditions. Possible solvents of this type are, preferably carboxylic acids with 1 to 6 carbon atoms, such as acetic acid, propionic acid or formic acid.

The first stage of the process according to the invention is carried out with the aid of a strong inorganic acid. Strong inorganic acids include, preferably, the hydrogen halide acids, such as hydrochloric acid and hydrobromic acid, and concentrated sulphuric acid.

The reaction temperatures can be varied within a substantial range in carrying out this process stage. In general, the reaction is carried out at a temperature between $-20°$ and $+50°$ C., preferably between $0°$ and $+40°$ C.

In carrying out the first stage of the process according to the invention, 1 to 10 moles of inorganic acid are preferably employed per mole of halogenopivaloyl cyanide of the formula (II).

The second stage of the process according to the invention is preferably carried out directly in the solution obtained from the first stage, i.e. without prior intermediate isolation of the halogenated trimethylpyruvic acid amides of the formula (IIIa) and after hydrolysis thereof in the customary manner to give the free acids of the formula (IIIb). The compounds (IIIa) and (IIIb) are also novel.

The second stage of the process according to the invention is carried out in aqueous solution or in the presence of an aqueous-acid solution, such as a solution containing a hydrogen halide acid (preferably hydrochloric acid) or sulphuric acid.

If the reaction is carried out in the presence of an organic solvent, any of the customary organic solvents can be used (such as, in particular, dimethylformamide).

The reaction temperatures can be varied within a substantial range in carrying out the second stage of the process according to the invention. In general, the reaction is carried out between $0°$ and $120°$ C., preferably between $0°$ and $100°$ C.

In carrying out the second stage of the process according to the invention, the starting substances are preferably employed in molar amounts, or an excess of compounds of the formula (IV) is employed. The intermediate products of the formula (V) are isolated in the customary manner.

The third stage of the process according to the invention is carried out in the presence of a base. The bases preferably employed are alkali hydroxides, (such as sodium hydroxide) in aqueous solution or alkali metal alcoholates (such as sodium methylate), in which case excess alcohol is used as the solvent.

The reaction temperatures can be varied within a substantial range in carrying out the third stage of the process according to the invention. In general, the reaction is carried out at a temperature between $0°$ and $100°$ C., preferably between $0°$ and $50°$ C.

In carrying out the third stage of the process according to the invention, 1 to 1.5 moles of alkylating agent are preferably employed per mole of intermediate product of the formula (V). The intermediate products or end products of the formula (Ia) are isolated in the customary manner.

Preferred possible diluents for the fourth stage of the process according to the invention are organic solvents (such as, preferably, isopropanol/glacial acetic acid).

The reaction temperatures can be varied within a substantial range in carrying out the fourth stage of the process according to the invention. The reaction is in general carried out at a temperature between $20°$ and $180°$ C., preferably between $40°$ and $150°$ C.

In carrying out the fourth stage of the process according to the invention, 1 to 3 moles of amine of the formula (VI) are preferably employed per mole of the compound of the formula (Ia). The end products are isolated in the customary manner.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

In addition to a very good general herbicidal action, the active compounds according to the invention are well-tolerated by useful plants. It is thus possible selectively to combat important harmful grasses in important crop plants, such as, for example, corn, soy beans, cotton and cereals.

The active compounds can be converted to the customary formulations, such as solutions, emulsions, wettable powders, suspensions, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.1 and 10 kg of active compound per ha, preferably between 0.1 and 5 kg/ha.

The present invention also provides a herbicidal composition containing as active ingredient a compound of the present invention in admixture with a solid diluent or carrier or in admixture with a liquid diluent or carrier containing a surface-active agent.

The present invention further provides a method of combating weeds, characterized in that there is applied to the weeds, or to a habitat thereof, a compound of the present invention alone or in the form of a composition containing as active ingredient a compound of the present invention, in admixture with a diluent or carrier.

The present invention yet further provides crops characterized by being protected from damage by weeds by being grown in areas in which immediately prior to and/or during the time of growing a compound of the present invention was applied, alone or in admixture with a diluent or carrier.

The examples which follow serve to further illustrate the invention.

PREPARATIVE EXAMPLES

Example 1

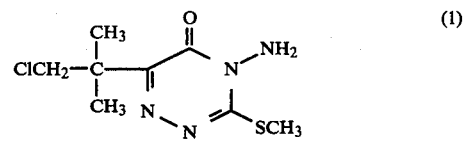

(1)

2.31 kg (15.88 moles) of chloropivaloyl cyanide were added to 9 liters of a solution of hydrogen bromide in glacial acetic acid (33% strength) at room temperature, while stirring. The mixture was subsequently stirred at room temperature for 4 hours. 288 ml (15.88 moles) of water were then added at 7° to 10° C. (exothermic reaction, about 37° C.) and the mixture was subsequently stirred at room temperature for 3 hours. Thereafter, the reaction solution was introduced into a mixture of 2.03 kg of thiocarbohydrazide and 15.9 liters of 1 N hydrochloric acid at 7° to 10° C. (highly exothermic reaction). This reaction mixture was subsequently stirred at 7° to 10° C. for 2 hours and at room temperature for 14 hours. Thereafter, the crystals which had precipitated were filtered off, washed with water and dried. 2,995 g (80.4% of theory) of crude 4-amino-6-chloro-tert.-butyl-3-mercapto-1,2,4-triazin-5-one of melting point 202°–208° C. were obtained.

2,813.4 g (12 moles) of the 4-amino-6-chloro-tert.-butyl-3-mercapto-1,2,4-triazin-5-one thus obtained were dissolved in 15 liters of 1 N sodium hydroxide solution. After the product had dissolved completely, 1,873.6 g of methyl iodide were added dropwise at 7° to 10° C. When the addition had ended, the mixture was subsequently stirred at 7° to 10° C. for 2 hours and at room temperature overnight. Thereafter, the solid which had formed was filtered off, washed with water and dried.

1,938 g (65% of theory) of 4-amino-6-chloro-tert.-butyl-3-methyl-thio-1,2,4-triazin-5-one of melting point 98° C. were obtained.

Preparation of the starting material

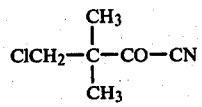

8,300 g (49.5 moles) of 92.5% pure β-chloropivaloyl chloride were warmed to 100° C., and 4,950 g (50 moles) of trimethylsilyl cyanide were added in the course of about 2 hours. The trimethylsilyl chloride formed was simultaneously distilled off. When the addition had ended, the temperature was increased slowly to 140° C. and the mixture was stirred at this temperature for about 1.5 hours. The reaction mixture was then distilled in vacuo. 7,500 g of β-chloropivaloyl cyanide of boiling point 62°–65° C./16 mbars were obtained.

Example 2

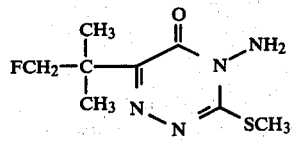

Starting from fluoropivaloyl cyanide, in a manner corresponding to that in Example 1, first crude 4-amino-6-fluoro-tert.-butyl-3-mercapto-1,2,4-triazin-5-one was obtained in 80% yield and was reacted further with methyl iodide to give 4-amino-6-fluoro-tert.-butyl-3-methyl-thio-1,2,4-triazin-5-one of melting point 121°–122° C., likewise in 80% yield.

Example 3

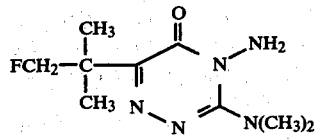

13.6 g (0.3 mole) of dimethylamine were introduced into a mixture of 350 ml of isopropanol and 12 g of glacial acetic acid, while cooling with ice. 21.8 g (0.1 mole) of 4-amino-6-fluoro-tert.-butyl-3-methylthio-1,2,4-triazin-5-one (obtained as described in Example 2) were then added to this reaction solution. The mixture was allowed to warm to room temperature and was then heated under reflux for 15 hours. Thereafter, the reaction mixture was concentrated and the oily residue was stirred into water. The mixture was extracted with methylene chloride and the extract was dried over sodium sulphate and concentrated. The oily residue was taken up in diisopropyl ether, seed crystals were added and the solid which crystallized out was filtered off and dried. 15.9 g (69% of theory) of 4-amino-3-dimethylamino-6-fluoro-tert.-butyl-1,2,4-triazin-5-one of melting point 86°–87° C. were obtained.

Example 4

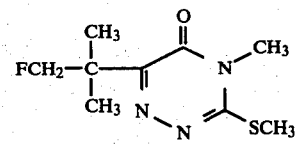

15 g (0.116 mole) of fluoropivaloyl cyanide were added dropwise to 92.8 g of a solution of hydrogen bromide in glacial acetic acid (33% strength) at room temperature, while stirring. When the addition had ended, the mixture was subsequently stirred at room temperature for 2 hours. 1.1 g (0.06 mole) of water were then added dropwise (exothermic reaction) and the mixture was subsequently stirred at room temperature for 3 hours. Thereafter, it was concentrated at 30° C. in vacuo. The residue was dissolved in 23 ml of dimethylformamide and the solution was added, under reflux, to 12.8 g (0.116 mole) of 4-methyl-thiosemicarbazide in 232 ml of water. The mixture was stirred under reflux for 48 hours and the crystals which had precipitated were then filtered off. After trituration with ligroin/petroleum ether and purification by column chromatography, 11 g (44% of theory) of 6-fluoro-tert.-butyl-3-mercapto-4-methyl-1,2,4-triazin-5-one of melting point 179°–80° C. were obtained.

5.4 g (0.024 mole) of the 6-fluoro-tert.-butyl-3-mercapto-4-methyl-1,2,4-triazin-5-one thus obtained were dissolved in 0.96 g (0.024 mole) of sodium hydroxide in 14 ml of water. After the product had completely dissolved, 3.9 g (0.028 mole) of methyl iodide were added dropwise. The mixture was stirred overnight at room temperature. Thereafter, the solid which had formed was filtered off, washed with water and dried. After purification by column chromatography, 4 g (73% of theory) of 6-fluoro-tert.-butyl-4-methyl-3-methylthio-1,2,4-triazin-5-one of melting point 102°–04° C. were obtained.

The compounds of the general formula (I)

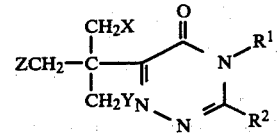

in which radicals X, Y, Z, $R^1$ and $R^2$ have the meanings listed in Table 1 which follows were obtained in an analogous manner and by the process according to the invention:

TABLE 1

| Compound No. | X | Y | Z | $R^1$ | $R^2$ | Melting point M.p. (°C.) |
|---|---|---|---|---|---|---|
| 5 | F | H | H | $NH_2$ | $-SC_2H_5$ | 80–83 |
| 6 | Cl | H | H | $NH_2$ | $-SC_2H_5$ | 93–96 |
| 7 | F | F | H | $NH_2$ | $-SCH_3$ | 122–24 |
| 8 | F | F | H | $NH_2$ | $-SC_2H_5$ | 100–03 |
| 9 | F | F | H | $NH_2$ | $-SC_3H_7$ | 110–12 |
| 10 | F | H | H | $NH_2$ | $-NHCH_3$ | 210–12 |
| 11 | F | H | H | $NH_2$ | $-NHC_2H_5$ | 118–20 |
| 12 | Cl | H | H | $NH_2$ | $-NHCH_3$ | 137–40 |
| 13 | Cl | H | H | $NH_2$ | $-N(CH_3)_2$ | 90–91 |
| 14 | Cl | H | H | $NH_2$ | $-NHC_2H_5$ | 103–06 |
| 15 | F | F | H | $NH_2$ | $-NHCH_3$ | 199–200 |
| 16 | F | F | H | $NH_2$ | $-N(CH_3)_2$ | 92–94 |
| 17 | F | F | H | $NH_2$ | $-NHC_2H_5$ | 146–48 |

TABLE 1-continued

| Compound No. | X | Y | Z | R¹ | R² | Melting point M.p. (°C.) |
|---|---|---|---|---|---|---|
| 18 | Cl | H | H | NH₂ | —NHC₃H₇ | 96–98 |
| 19 | Br | H | H | NH₂ | —SCH₃ | 109–10 |
| 20 | F | H | H | NH₂ | —NHC₃H₇ | 106–08 |
| 21 | F | F | H | NH₂ | —NHC₃H₇ | 70–72 |
| 22 | F | H | H | NH₂ | —NH(CH₂)₅CH₃ | 93–96 |
| 23 | Cl | H | H | NH₂ | —NH(CH₂)₅CH₃ | 99–104 |

The herbicidal activity of the compounds according to this invention was illustrated by the following biological test example, in which the active compounds are each identified by the number (given in brackets) from the preparative examples and Table 1 herein above. The known comparison compound is identified as follows:

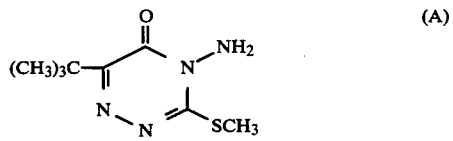

4-amino-3-methylthio-6-tert.-butyl-1,2,4-triazin-5-one (known, for example, from U.S. Pat. No. 3,671,523).

Example 5

Pre-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0% = no action (like untreated control)
100% = total destruction

In this test, for example, the compounds (1) and (2) exhibited a better selectivity in corn, cotton and wheat than the compound (A) known from the prior art, while having a comparably good activity.

Example 6 field experiments

Pre-emergence test/test in the open
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Shortly after sowing the test plants in the open, the individual plots were watered with the amount of the active compound preparation required for uniform wetting of the soil surface. The concentration of the active compound in the preparation was of no importance, only the amount of active compound applied per unit area being decisive.

After 5 weeks, the degree of damage to the test plants was rated in % damage in comparison to the development of the untreated control. The figures denoted:

0% = no action
100% = total destruction.

In this test, in particular, compound (1) showed a considerably better selectivity in corn than the compound (A) known from the prior art, while having an equally good activity.

It will be understood that the specification and examples are illustrative but not limitative of the present invention and that other embodiments within the spirit and scope of the invention will suggest themselves to those skilled in the art.

We claim:

1. A substituted 6-halogeno-tert.-butyl-1,2,4-triazin-5-one of the formula

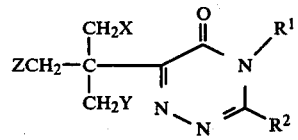

in which
R¹ is an amino or methyl group,
R² is a $C_{1-4}$-alkylmercapto, $C_{1-6}$-alkylamino or di-($C_{1-6}$)-alkylamino group,
X is a halogen atom, and
Y and Z each independently is a hydrogen or halogen atom.

2. A compound according to claim 1, in which
R² is a methylmercapto, ethylmercapto, propylmercapto, methylamino, ethylamino, propylamino, hexylamino, dimethylamino, diethylamino or methylethylamino group,
X is a fluorine, chlorine, or bromine atom, and
Y and Z each independently is a hydrogen, fluorine, chlorine or bromine atom.

3. A compound according to claim 1, wherein such compound is 4-amino-6-chloro-tert.-butyl-3-methylmercapto-1,2,4-triazin-5-one of the formula

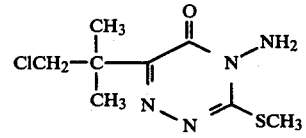

4. A compound according to claim 1, wherein such compound is 4-amino-6-fluoro-tert.-butyl-3-methylmercapto-1,2,4-triazin-5-one of the formula

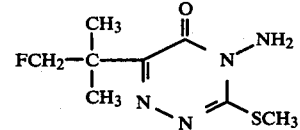

5. A compound according to claim 1, wherein such compound is 4-amino-6-chloro-tert.-butyl-3-ethylmercapto-1,2,4-triazin-5-one of the formula

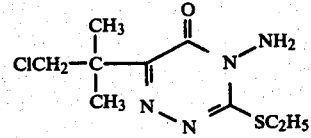

6. A compound according to claim 1, wherein such compound is 4-amino-6-fluoro-tert.-butyl-3-methylamino-1,2,4-triazin-5-one of the formula

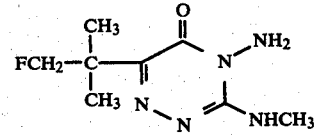

7. A herbicidal composition, comprising a herbicidally effective amount of a compound according to claim 1 in admixture with a solid diluent.

8. A method of combating weeds, comprising applying to the weeds, or to a habitat thereof, a herbicidally effective amount of a compound according to claim 1.

9. The method according to claim 8, wherein such compound is
4-amino-6-chloro-tert.-butyl-3-methylmercapto-1,2,4-triazin-5-one,
4-amino-6-fluoro-tert.-butyl-3-methylmercapto-1,2,4-triazin-5-one,
4-amino-6-chloro-tert.-butyl-3-ethylmercapto-1,2,4-triazin-5-one,
4-amino-6-fluoro-tert.-butyl-3-methylamino-1,2,4-triazin-5-one,
4-amino-6-fluoro-tert.-butyl-3-dimethylamino-1,2,4-triazin-5-one,
4-amino-6-bromo-tert.-butyl-3-methylmercapto-1,2,4-triazin-5-one,
4-amino-6-(1,1-[bis-fluoromethyl]-ethyl)-3-methylamino-1,2,4-triazin-5-one.

10. A compound according to claim 1, wherein such compound is 4-amino-6-fluoro-tert.-butyl-3-dimethylamino-1,2,4-triazin-5-one of the formula

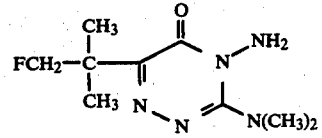

11. A compound according to claim 1, wherein such compound is 4-amino-6-bromo-tert.-butyl-3-methylmercapto-1,2,4-trazin-5-one of the formula

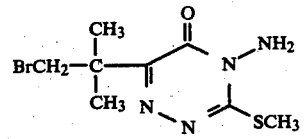

12. A compound according to claim 1, wherein such compound is 4-amino-6-(1,1-[bis-fluoromethyl]-ethyl)-3-methylamino-1,2,4-triazin-5-one of the formula

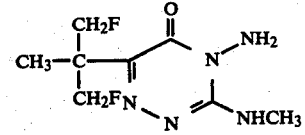

* * * * *